United States Patent
Palkhiwala

(10) Patent No.: US 6,361,799 B1
(45) Date of Patent: Mar. 26, 2002

(54) CLUMP-FREE LIQUID DISPERSIBLE POWDER COMPOSITIONS AND PROCESS FOR MAKING THE SAME

(75) Inventor: Burgise F. Palkhiwala, East Windsor, NJ (US)

(73) Assignee: Accumed Inc., Lawrenceville, NJ (US)

( * ) Notice: Subject to any disclaimer, the term of this patent is extended or adjusted under 35 U.S.C. 154(b) by 0 days.

(21) Appl. No.: 09/691,441

(22) Filed: Oct. 18, 2000

(51) Int. Cl.$^7$ .............................. A61K 9/14; A61K 9/16
(52) U.S. Cl. ..................... 424/489; 424/498; 424/490
(58) Field of Search ................. 424/489, 498, 424/490

(56) References Cited

U.S. PATENT DOCUMENTS

| | | | |
|---|---|---|---|
| 4,459,280 A | 7/1984 | Colliopoulos et al. | 424/35 |
| 4,551,331 A * | 11/1985 | Rudin | 424/195.1 |
| 4,626,287 A | 12/1986 | Shah et al. | 106/197.1 |
| 4,671,823 A | 6/1987 | Shah et al. | 106/197.1 |
| 5,149,541 A | 9/1992 | Leis, Jr. et al. | 424/489 |
| 5,219,570 A | 6/1993 | Barbera | 424/195.1 |
| 5,834,026 A * | 11/1998 | Lu | 424/498 |

* cited by examiner

*Primary Examiner*—Thurman K. Page
*Assistant Examiner*—Rachel M. Bennett
(74) *Attorney, Agent, or Firm*—Watov & Kipnes, P.C.; Kenneth Watov

(57) ABSTRACT

A powder composition which is readily dispersible in a liquid such as water without clumping, comprises a powder the particles of which are uniformly coated with an effective amount of a surfactant, preferably Polysorbate-80, sufficient to enable the powder composition to readily disperse in the liquid. A process for making the powder composition that disperses readily in a liquid without clumping, comprises the step of continuously mixing a powder with an amount of a surfactant for a time sufficient to uniformly coat at least substantially all of the particles of the powder with the surfactant.

6 Claims, 1 Drawing Sheet

CLUMP-FREE LIQUID DISPERSIBLE POWDER COMPOSITIONS AND PROCESS FOR MAKING THE SAME

FIELD OF THE INVENTION

The present invention relates generally to compositions which can disperse rapidly in liquid and a process for making the composition, and more particularly a clump-free powder composition which mixes readily and uniformly in water or other liquids, and to a process of making such powder compositions.

BACKGROUND OF THE INVENTION

Various liquid soluble or dispersible powder products exist which are suitable for human consumption. Examples of such products include, among others, medications, flavoring agents, functional food products such as vitamin and nutrient supplements, and beverage products. Such products also facilitate efficient absorption in the body of associated ingredients, when first dissolved in liquid prior to consumption. Palatability of such products may be easily enhanced by combining the products with flavorings, sweeteners, or effervescent agents. Powder products are much easier and cheaper to handle, ship and store compared with liquid-containing products, and are also less perishable. Typically, all that is required prior to use or consumption is rehydration, for example.

Powder products especially those composed of fine particles or particulates, often resist wetting due to their inherently dry nature. As such, they can be difficult to disperse or dissolve in water or other liquids. The powder particles have a tendency to clump or agglomerate which further diminishes the product's dispersibility. One type of powder product of particular concern that is especially prone to this problem is powder bulk laxatives. Such bulk laxatives are composed of bulking agents including, but not limited to dietary bulk fibers, husks of grains, psyllium powder, cellulose derivatives, cellulose ethers such as carboxymethylcellulose and methyl cellulose, polysaccharide-based materials, and the like. The laxative properties of these bulking agents are due largely in part to their hydrophilic properties and to their mucilaginous character when wetted. Such materials relieve constipation by increasing the bulk and moisture content of the stool, and promoting a lubricating effect on the stool. The most commonly available bulking agents are psyllium and methyl cellulose.

Due to the same laxative properties of such products, powder bulk laxatives inherently have especially poor wetting capability, and must be vigorously mixed with water for a considerable amount of time to produce a somewhat palatable and relatively uniform drink. The numerous individual particles tend to agglomerate or clump when in contact with water. Hydration takes place over the surface of such agglomerates to form gel-coated clumps, the interiors of which are still substantially dry, and these clumps are difficult to disperse. The effects are further aggravated by the tendency of such clumps to float on the surface of the water leading to further agglomeration. The resulting taste, appearance and organoleptic properties including texture and mouthfeel of such partially dissolved suspensions are often unacceptable to many users. The poor dispersibility or mixability of powder bulk laxatives becomes more pronounced at cooler temperatures.

One prior attempt at alleviating the problems described above has been to admix the bulking agents with high weight percentage amounts of sugar (typically about 50–80 percent weight of the total composition) or encrust each particle with a sugar layer. Another prior attempt at preventing clumps uses a spray-dry process, more specifically mixing psyllium powder with a solution containing a sugar such as maltodextrin. The wetted powder is then dried through a heating process. Although taste and dispersibility are improved in such products, the addition of a sugar may be problematic. For example, those suffering from blood sugar disorders, including diabetics and/or users who are on restricted diets may have difficulty taking such high sugar powder bulk laxative. In addition, considerable time and mixing is still required for complete clump-free dispersion. The cost of raw materials, storage, and processing is also significantly higher for sugar-added compositions.

Accordingly, it would be highly desirable to provide an edible powder composition including those comprising powder bulking agents, in which the composition when mixed in liquid is palatable, has desirable organoleptic properties and which may be administered without significant clumping. It would be desirable to implement a simple and safe process of making such compositions readily dispersible in a cost efficient manner with minimal processing requirements. It would be advantageous to implement a process which reduces the amount of raw material required, thus reducing the weight and volume of the resulting edible powder composition and the associated costs of processing, packaging, shipping and storage.

SUMMARY OF THE INVENTION

The present invention generally relates to a powder composition that disperses readily and uniformly in a given liquid without clumping. The composition particularly comprises an edible or non-edible powder coated uniformly throughout with an amount of a surfactant sufficient to uniformly disperse the powder in the liquid. A further aspect of the invention provides a process for making the edible powder composition which comprises the step of continuously mixing particles of the edible powder with an amount of a surfactant for a time sufficient to uniformly coat substantially all of the edible powder with the surfactant. As used herein the term "uniformly coated" shall mean that at least a substantial number of the particles are at least substantially coated with the surfactant.

In one aspect of the present invention there is provided a process for making a powder bulk laxative composition that disperses readily in water without clumping. The process comprises the step of continuously mixing a bulking agent mixture with effective amount of a surfactant for a sufficient time to uniformly coat at least substantially all the particles of the powdered bulking agent mixture with the surfactant.

In another aspect, the present invention is directed a powder laxative composition that disperses readily and uniformly in water without clumping. However, the invention is not meant to be limited to powder laxative compositions, or edible powders, and may be used to provide and make liquid dispersible non-edible powders.

The present invention is generally directed to powder composition which disperses readily in a liquid, and a process of making such compositions. The composition advantageously disperses in the water or other liquid in a uniform manner. The process of the present invention is especially directed to processing any edible powder product suitable for mixing in water or other liquids including beverage powders, milk powders, food additives, flavoring agents, pharmaceutical agents, coloring agents, soup mixes, preservatives, and the like.

The present invention is directed to a powder composition that disperses readily in a liquid without clumping, wherein in the examples given below, the composition comprises an edible powder, having particles uniformly coated with an effective amount of a surfactant.

The present invention is further directed to a process for making an edible powder composition that disperse readily in a liquid without clumping wherein the process comprises the step of continuously mixing edible or non-edible powder particles with an amount of a surfactant for a time sufficient to uniformly coat at least substantially all of the powder with the surfactant.

BRIEF DESCRIPTION OF THE DRAWINGS

Various embodiments of the invention are described below with reference to the following drawing.

DETAILED DESCRIPTION OF THE INVENTION

Figure 1:
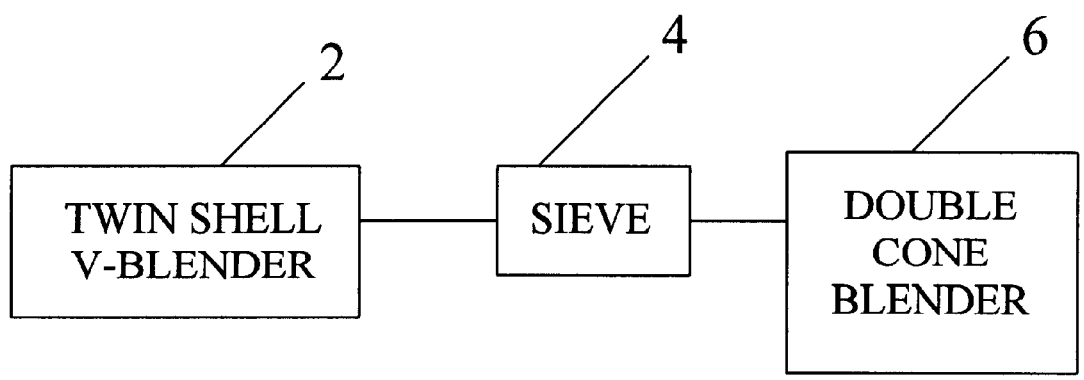
FIG. 1 is a block schematic diagram showing a system for one embodiment of the invention.

The powder composition of the present invention is preferably an edible powder composition and especially a bulk laxative powder product which contains bulking agent particles substantially coated with a surfactant. The term "bulking agent" as used herein corresponds to the active ingredient present in a bulk laxative product which functions to increase the bulk, water content or frequency of stools in users to whom it is administered. Such bulking agents include, but are not limited to, dietary bulk fibers, husks of grains, psylliumi powder, cellulose derivatives including cellulose ethers, carboxymethylcellulose, methyl cellulose, polysaccharide-based materials, and the like.

Preferably, the bulking agent should be both dry and in powder form. The term "dry" does not mean free of water in the absolute sense but rather substantially free of water so that the individual particles do not adhere to one another and so that the powder flows easily when poured. The term "powder" as used herein includes very fine, dust-like particles or particulates as the term is understood by those skilled in the art.

Surfactants are molecules comprising a structure having a head end and tail end. The head end is typically hydrophilic (water-loving). The tail end is typically hydrophobic (water-hating). In the present invention, the surfactant forms a coating on substantially all of the particles of the bulking agent mixture sufficient to prevent clumping. The surfactant acts as a link between water and the bulking agent particles for increasing dispersibility at the liquid-solid interface, and loosens the particles of the bulking agents from one another or other surfaces, thus preventing agglomeration and clumping normally observed between adjacent uncoated bulking agent particles. The link facilitates rapid dispersion and slightly delays hydration of the powder bulking agents, thus preventing rapid surface hydration prior to complete dispersion and substantially minimizing formation of clumps. The surfactant due to the two component molecular structure reduces the surface tension and the adhesive force of the water, thereby increasing wetting capacity and reducing the wetting resistance of the powder bulking agent. These effects thus promote rapid dispersion of the bulking agents in the water during hydration for a clump-free product. Surfactants fall into several classes including those which are anionic, ionic, cationic and amphoteric.

Preferred surfactants are non-ionic surfactants. Particularly preferred surfactants are sorbitan esters (SPAN® available from ICI Americas, Inc.) and polyoxyethylene sorbitan fatty acid esters or polysorbates (TWEEN® available from ICI Americas, Inc.) made from the reaction product of monoglycerides or sorbitan esters with ethylene oxides.

Examples of useful polysorbates include polyoxyethylene 20 mono- and diglycerides of saturated fatty acids, polyoxyethylene 4 sorbitan monostearate, polyoxyethylene 20 sorbitan tristearate, polyoxyethylene 20 sorbitan monooleate, polyoxyethylene 5 sorbitan monooleate, polyoxyethylene 20, sorbitan trioleate, sorbitan monopalmitate, sorbitan monolaurate, propylene glycol monolaurate, glycerol monostearate, diglycerol monostearate, glycerol lactylpalmitate. Most preferably, the surfactant is polyethylene 20 sorbitan monooleate or Polysorbate 80 (TWEEN 80 available from ICI Americas, Inc.).

The surfactant is typically present in the amount of from about 0.05 to 1.5 percent by weight of the total composition. More preferably, the composition comprises from about 0.1 to 0.9 percent by weight surfactant.

The process for making the powder composition of the present invention (e.g. a powder bulk laxative composition) includes mixing the bulking agents with the surfactant at ambient conditions for a time sufficient to permit the surfactant to uniformly coat the powder bulking agent.

In addition to the surfactant, other excipients or ingredients may be added prior to the addition of the surfactant in formulating the composition of the present invention. The compositions of the present invention may include one or more conventional ingredients such as, for example, lubricants, glidants, carriers, natural and artificial sweeteners, disintegrants, preservatives, flavoring and coloring agents, and the like, which may be added to the composition in the amount of from about 1% to 8% weight percent, typically from about 2% to 6% weight percent and most preferably to about 2% to 4% percent. If desired, the ingredients can also be added to the composition after the addition of the surfactant.

Suitable ingredients include binders such as acacia mucilage, starch mucilage pregelatinized starch, sodium alignate, starch paste, polyvinylpyrrolidone, dextrin, polyethylene glycol, guar gum, zein, and polymethacrylates.

Disintegrating agents include microcystalline cellulose (e.g. AVICEL ®), sodium carboxymethyl cellulose, cellulose gum, crosslinked providone, alginic acid and alginates, pregelatinized starch, sodium starch glycollate, corn starch, starch (e.g. potato/maize starch), and ion exchange resin such as polacrin potassium.

Examples of water-soluble fillers are: soluble lactose, compressible sugar, confectioners sugar, dextrose, mannitol, sodium chloride, sorbitol, xylitol. Examples of water-insoluble fillers are: calcium carbonate, magnesium carbonate, calcium phosphate (e.g. di and tri basic calcium phosphate), calcium sulphate, kaolin, microcystalline cellulose, powdered cellulose, pregelatinized starch, barium sulphate, magnesium trisilicate, aluminum hydroxide.

Generally, lubricants are used in as low an amount as possible. Examples of lubricants include: stearates (e.g. magnesium or calcium stearate), talc, polyethylene glycol, liquid paraffin, sodium lauryl sulphate, magnesium lauryl sulphate, colloidal silicone dioxide, palmitostearate, stearic acid, zinc stearate, hydrogenated vegetable oil.

Glidant examples include talc, starch, magnesium stearate, silica derivatives, such as colloidal silica (e.g. AEROSIL) pyrogenic silica, hydrated sodium silicoaluminate, colloidal silicon dioxide (AEROSIL 200).

Flavoring agents include orange, cherry, strawberry, raspberry, grape and apple flavors.

Sweetening agents, include for example, sodium saccharin, aspartame, confectioners sugar, sorbitol, xylitol and mixtures thereof.

It is noted that the ingredients, when present, are added in sufficient amount for their intended purpose. The determination of such an amount would be known to one of ordinary skill in the art.

The bulking agents, surfactants and the other ingredients in the composition are preferably uniformly mixed or blended. The mixing may be performed utilizing any available conventional mixing processes where close and thorough contact between the surfactant and the bulking agent is readily attained. Preferably the composition is mixed by agitation, preferably through the use of a high-speed mixer, tumbler, double cone blender, V-blender, and the like. Once the surfactant is thoroughly mixed with the bulking agents, the composition is then recovered and packaged. The resulting composition is comprised of from greater than 50 percent by weight bulking agent, greater than 0.05% by weight and preferable from about 0.5 to 1.5% by weight surfactant, with other ingredients forming the remainder.

A system for mixing a powder product and surfactant together, as used by the inventors is shown in FIG. 1. The system includes a Twin Shell V-Blender 2 of Patterson Kelly Co.; a sieve 4 for passing particles smaller than a designated size; and a Double Cone Blender 6 of Gemco, Inc. The sieve 4 is only required in applications where the powder particles must be kept smaller than a given size.

By way of the following examples the composition and process of the present invention will now be illustrated, however, the examples are not in any way meant to be limiting.

EXAMPLE 1

TABLE 1

| Ingredient: | Amount (kg) |
|---|---|
| 1) Methyl Cellulose- A 4M Premium | 89.474 |
| 2) Domino's Sugar Extra Fine Gran. NF | 694.083 |
| 3) Citric Acid Anhydrous USP/NF (Granular) | 32.300 |
| 4) FD&C Yellow #6 (Lake) 16% C:5285/W:9606 | 0.895 |
| 5) Orange Flavor - 66.167 SD | 14.146 |
| 6) Potassium Citrate Monohydrate USP (Granular) | 13.063 |
| 7) Riboflavin (Vitamin B2) NSP/NF | 0.089 |
| 8) Colloidal Silicon Dioxide (AEROSIL ® 200) NF | 2.125 |
| 9) Talc USP (Code #127) | 2.125 |
| 10) Polysorbate 80 (TWEEN ® 80) USP/NF | 1.7 |

A bulk laxative powder composition containing the ingredients and the amounts shown in Table 1 can be prepared in ambient conditions, using the system of FIG. 1, in the following manner:

44.737 kilograms of methyl cellulose is placed in the Twin Shell V-Blender 2, and blended with 0.895 kilogram of FD&C Yellow #6 and 0.089 kilogram of riboflavin as a premix for about 5 minutes. Next, 8.947 kilograms of sugar (sucrose) and 1.7 kilograms of Polysorbate 80 are added to the blended premix in the Twin Shell V-Blender 2, and blended for about 10 minutes. The mixture is then passed through a 20 mesh sieve, and unloaded into a tared, polythelene lined container and weighed. If actual weight of the mixture deviates more than 0.5% theoretical weight, a quality control investigation is made. The weighed mixture is then passed into a Double Cone Blender 6 for blending with 44.737 kilograms of methyl cellulose, 685.136 kilograms of sugar (sucrose), 32.3 kilograms of citric acid, 14.146 kilograms of orange flavor, 13.063 kilograms of potassium citrate, 2.125 kilograms of colloidal silicon dioxide for about 20 minutes. Then add 2.125 kilograms of talc and blend for 2 minutes. Collect the final blend into suitable tared containers lined with two clean polythelene bags.

EXAMPLE 2

TABLE 2

| Ingredient: | Amount (kg) |
|---|---|
| 1) Psyllium 95% Fine Powder- 60 mesh USP | 410.345 |
| 2) Aspartame | 5.310 |
| 3) Citric Acid Anhydrous USP/NF (Granular) | 38.500 |
| 4) FD&C Yellow #6 (Soluble Color) | 0.302 |
| 5) Orange Flavor - 66.167 SD | 21.000 |
| 6) Maltodextrin NF Grade (580) | 223.602 |
| 7) D&C Yellow #10 K7059 | 0.241 |
| 10) Polysorbate 80 (TWEEN ® 80) USP/NF | 0.70 |

A bulk laxative powder composition containing the ingredients and the amounts shown in Table 2 was prepared at ambient conditions in the following manner:

38.5 kilograms of citric acid, 4.828 kilograms of maltodextrin, 0.302 kilograms of FD&C Yellow #6, 0.241 kilograms of D&C #10, 5.31 kilograms of aspartame, and 0.700 kilograms of Polysorbate-80 are placed into the Twin Shell V-Blender 2 and blended together into a premix for about 5 minutes. The blended premix is then passed through a 20 mesh sieve 4, and unloaded into a tared, polythelene lined container and weighed. If actual weight of the mixture deviates more than 0.5% theoretical weight, then a quality control recheck is made. The weighed mixture is then passed into a Double Cone Blender for blending with 410.345 kilograms of psyllium powder, 218.774 kilograms of maltodextrin, and 21.000 kilograms of orange flavor for about 20 minutes. The final blend is collected into suitable tared containers lined with two clean polythelene bags.

EXAMPLE 3

TABLE 3

| Ingredient | Amount (kg) |
|---|---|
| 1) Psyllium 95% Fine Powder - 60 mesh USP | 198.3333 |
| 2) Domino's Sugar Extra Fine Granulated NF | 470.8667 |
| 3) D&C Yellow #10 K7059 | 0.350 |
| 4) FD&C Yellow #6 (Soluble Color) | 0.350 |
| 5) Orange Flavor - 66.167 SD | 14.000 |
| 6) Citric Acid Anhydrous USP/NF (Granular) | 15.400 |
| 7) Polysorbate 80 (Tween 80) USP/NF | 0.700 |

A bulk laxative powder composition containing the ingredients and the amounts shown in Table 3 was prepared at ambient conditions in the following manner:

15.4 kilograms of citric acid, 4.9 kilograms of sugar (sucrose), 0.350 kilogram of D&C Yellow #10 K7059, 0.350 kilogram of FD&C Yellow #6 and 0.700 kilogram of Polysorbate 80 are placed into the Twin Shell V-Blender 2 and blended together into the premix for about 5 minutes. The blended premix is then passed through a 20 mesh sieve 4 and unloaded into a tared polythelene lined container and weighed. If actual weight of the mixture deviates more than 0.5% of theoretical weight, then a quality control recheck is made. The weighed mixture is then passed into a Double Cone Blender for blending with 198.3333 kilograms of psyllium powder, 465.9667 kilograms of sugar (sucrose) and 14.0 kilograms of Orange flavor for about 20 minutes. The final blend is collected into suitable tared containers lined with two clean polythelene bags.

EXAMPLE 4

TABLE 4

| Ingredient: | Amount (kg) |
| --- | --- |
| 1) Methyl Cellulose- A 4M Premium | 137.2549 |
| 2) Maltodextrin NF Grade (580) | 453.8127 |
| 3) DL-Maltic Acid | 49.4118 |
| 4) Aspartame | 6.3137 |
| 5) Dicalcium Phosphate Anhydrous | 3.4314 |
| 6) FD&C Yellow #6 (Lake) 16% C:5285/W:9606 | 1.3725 |
| 7) Orange Flavor - 66.167 SD | 23.4706 |
| 8) Potassium Citrate Monohydrate USP (Granular) | 20.0392 |
| 9) Riboflavin (Vitamin B2) NSP/NF | 0.3431 |
| 10) Colloidal Silicon Dioxide (AEROSIL ® 200) NF | 1.75 |
| 11) Talc USP (Code #127) | 1.75 |
| 12) Polysorbate 8 (TWEEN ® 80) USP/NF | 1.05 |

A bulk laxative powder composition containing the ingredients and the amounts shown in Table 3 was prepared at ambient conditions in the following manner:

13.725 kilograms of maltodextrin, 6.314 kilograms of Aspartame, 1.373 kilograms of FD&C Yellow #6, 3.431 kilograms of dicalcium phosphate, and 1.05 kilograms of Polysorbate-80 are placed into Twin Shell V-Blender 2 and blended together into a premix for about 5 minutes. The blended premix is passed through a 20 mesh sieve 4, and unloaded into a tared, polythelene lined container and weighed. If actual weight of the mixture deviates more than 0.5% theoretical weight, then a quality control recheck is made. The weighed mixture is then passed into a Double Cone Blender 6 for blending with 137.255 kilograms of methyl cellulose, 440.0877 kilograms of maltodextrin, 49.412 kilograms of malic acid, 20.039 kilograms of potassium citrate monohydrate, 23.471 kilograms of orange flavor, and 1.75 kilograms of colloidal silicon dioxide for about 20 minutes. Next, 1.75 kilograms of talc is added to the final mixture and blended for 3 minutes. The final blend is collected into suitable tared containers lined with two clean polythelene bags.

EXAMPLE 5

TABLE 5

| Ingredient: | Amount (kg) |
| --- | --- |
| 1) Psyllium 95%, 40 mesh USP | 340.000 |
| 2) Cerelose Dextrose | 344.100 |
| 3) Citric Acid Anhydrous USP/NF (Granular) | 14.500 |
| 4) Polysorbate 80 (TWEEN ® 80) USP/NF | 1.40 |

A bulk laxative powder composition containing the ingredients and the amounts shown in Table 4 was prepared at ambient conditions in the following manner:

45.5 kilograms of cerelose dextrose is placed into a Twin Shell V-Blender 2 and blended with 14.5 kilograms of citric acid and 1.40 kilograms of Polysorbate-80 into a premix for about 5 minutes. The blended premix is passed through a 20 meshp sieve, and unloaded into a tared, polythelene lined container and weighed. If actual weight of the mixture deviates more than 0.5% theoretical weight, then a quality control recheck is made. The weighed mixture is then passed into a Double Cone Blender 6 for blending with 340.0 kilograms of psyllium powder, and 298.60 kilograms of cerelose dextrose for about 20 minutes. The final blend is collected into suitable tared containers lined with two clean polythelene bags.

Although various embodiments of the invention have been shown and described, they are not meant to be limiting. Those of skill in the art may recognize various modifications to these embodiments, which modifications are meant to be covered by the spirit and scope of the appended claims.

What is claimed is:

1. A process for making a powder composition that disperses readily in water without clumping, comprising the step of continuously mixing particles of a powder with an amount of at least one surfactant selected from the group consisting of sorbitan esters and polyoxyethylene derivatives of sorbitan fatty acid esters in the absence of a solvent for the surfactant, for a time sufficient to uniformly coat at least substantially all particles of the powder with said surfactant.

2. The process of claim 1, wherein the powder composition is selected from the group consisting of dietary bulk fibers, psyllium, cellulose ethers, methyl cellulose, carboxymethylcellulose, and mixtures thereof.

3. The process of claim 1, wherein the amount of the surfactant is in the range of from about 0.05 to 1.5 percent by weight, based on the total weight of the composition.

4. The process of claim 3, wherein the amount of the surfactant is in the range of from about 0.1 to 0.9 percent by weight.

5. The process of claim 1, wherein the surfactant is polyethylene 20 sorbitan monooleate or Polysorbate-80.

6. The process of claim 1 wherein the powder composition is a powder laxative composition.

* * * * *